United States Patent [19]

Hall

[11] 4,328,169

[45] May 4, 1982

[54] PROCESS FOR THE PREPARATION OF VINYLCYCLOPROPANE DERIVATIVES

[75] Inventor: Allen L. Hall, Amelia, Ohio

[73] Assignee: Emery Industries, Inc., Cincinnati, Ohio

[21] Appl. No.: 200,750

[22] Filed: Oct. 27, 1980

[51] Int. Cl.³ .................. C07C 121/48; C07C 49/533; C07C 69/743; C07C 103/19

[52] U.S. Cl. .................. 260/465 K; 548/190; 548/200; 260/454; 548/201; 548/202; 260/456 R; 548/206; 548/213; 260/456 P; 548/214; 548/225; 260/464; 548/233; 548/235; 260/465 D; 548/236; 548/243; 260/465 F; 548/245; 548/247; 260/465 G; 548/248; 548/337; 260/465 H; 548/338; 548/341; 260/961; 548/346; 548/373; 546/139; 548/375; 548/378; 546/143; 549/49; 549/51; 546/144; 549/57; 549/58; 546/145; 549/61; 549/62; 546/146; 549/70; 549/71; 546/152; 549/74; 549/78; 546/168; 549/80; 560/18; 546/169; 560/21; 560/59; 546/170; 560/102; 560/124; 546/173; 564/152; 564/155; 546/174; 564/190; 546/178; 568/27; 568/28; 546/179; 568/31; 568/33; 546/180; 568/34; 568/58; 546/286; 568/67; 568/631; 546/290; 568/635; 548/924; 546/314; 548/928; 548/939; 546/330; 548/949; 548/939; 546/340; 568/949; 548/445; 546/342; 548/467; 548/469; 546/350; 548/524; 548/525; 548/182; 548/518; 548/560; 549/471; 549/472

[58] Field of Search .................. 260/456 R, 454, 464, 260/465 K, 961; 560/102, 124; 564/152, 155, 190; 568/14, 27, 28, 312, 314, 316, 346, 348, 356, 924, 949

[56] References Cited

U.S. PATENT DOCUMENTS 3,974,199  8/1976  Plonka et al. .................. 260/464

OTHER PUBLICATIONS

Skinner et al., J. Am. Chem. Soc., 72, 1648 (1950).
Kierstead et al., J. Chem. Soc., 1952, 3610–3621.
Kierstead et al., J. Chem. Soc., 1953, 1799.
Murdock et al., J. Org. Chem., 27, 2395 (1962).
Birch et al., J. Org. Chem., 23, 1390 (1958).
Schmid et al., J. Org. Chem., 32, 254 (1967).
Stewart et al., J. Org. Chem., 34, 8 (1969).

*Primary Examiner*—Dolph H. Torrence
*Attorney, Agent, or Firm*—Kenneth D. Tremain

[57] ABSTRACT

This invention provides a convenient and commercially adaptable process for the preparation of vinylcyclopropane derivatives in high yield. For the process an alkylating agent and activated methylene compound are reacted in the presence of an alkylene oxide derivative and alkali metal compound. Water can also be present and/or the reaction may be carried out in an inert organic diluent.

9 Claims, No Drawings

PROCESS FOR THE PREPARATION OF VINYLCYCLOPROPANE DERIVATIVES

BACKGROUND OF THE INVENTION

G. S. Skinner et al. first reported the condensation of 1,4-dihalo-2-butene and diethyl malonate in J. Am. Chem. Soc., 72, 1648 (1950). The condensation was conducted under anhydrous conditions by reacting the dihalide with the pre-formed disodio anion of the malonic ester in an attempt to synthesize spirocyclopentane-1,5'-barbiturates. Kierstead et al. (J. Chem. Soc., 1952, 3610–21 and J. Chem. Soc., 1953, 1799) reported the preparation of diethyl 2-vinylcyclopropane-1,1-dicarboxylate by the condensation of 1,4-dibromo-2-butene and ethyl sodiomalonate and observed that continual attack by malonate anion on the 2-vinylcyclopropane derivative produced side products, one of which was 2-vinylbutane-1,1,4,4-tetracarboxylate. Kierstead et al. also extended the general reaction to ethyl cyanoacetate and ethyl acetoacetate to obtain the corresponding 2-vinylcyclopropane derivatives. In an attempt to develop a new synthetic route for the preparation of the cyclopentane counterparts of deoxyribonucleosides, Murdock et al. in J. Amer. Chem. Soc., 27, 2395 (1962) reported condensing cis-1,4-dichlorobutene-2 with sodiomalonic ester under anhydrous conditions as the first step in their reaction sequence.

With all of the above reactions, as well as in other reports dealing with the condensation of malonic esters with 1,4-dihalo-2-butenes, e.g. Birch et al., J. Org. Chem., 23, 1390(1958); Schmid et al., J. Org. Chem., 32, 254 (1967); Stewart et al., J. Org. Chem., 34, 8 (1969), the metal alkoxide and malonic ester were prereacted to first form the corresponding sodiomalonate anion, which was then very slowly added to the dihalobutene. This procedure was considered essential for the successful conduct of the reaction and to optimize the yield of the vinylcyclopropane dicarboxylate. The dihalo compound was not combined directly with the alcoholic caustic to avoid ether by-product formation since this is a well known and widely used procedure (Williamson synthesis) for the preparation of ethers. By adding the malonate anion to the dihalobutene and carefully controlling the rate of this addition, it was believed that linear diaddition products formed by either continued attack of the vinylcyclopropane product by malonate anion or reaction of both the halogens on a single molecule would be minimized. Strictly anhydrous conditions were employed throughout the entire reaction procedure, i.e. during the formation of the anion and the addition of the anion to the dihalobutene, since it is generally accepted that for malonate and acetoacetic ester condensations the presence of water is detrimental (Practical Organic Chemistry, A. I. Vogel, 3rd Ed., Longmans, Green and Co., Ltd., London (1967) pp. 481–486). Even as late as 1970 the classical procedure first developed by Skinner and coworkers was still being used as evidenced by the report of Den Besten et al. (J. Chem. Eng. Data, 15, 453 (1970)) who prepared diethyl 2-vinylcyclopropane-1,1-dicarboxylate for subsequent thermal decomposition.

In view of the complex state of the reagents, the requirement to operate under strictly anhydrous conditions and the necessity for a sophisticated reaction vessel to carry out the detailed addition, it has heretofore not been practical to prepare vinylcyclopropane derivatives on a commercial scale via such condensation reactions. It would be highly desirable therefore, if an improved process for the preparation of dialkyl 2-vinylcyclopropane-1,1-dicarboxylates by the reaction of 1,4-dihalobutenes and malonic esters were available. It would be even more desirable if the process was adaptable to commercial operation and if it could be extended to the preparation of a wide variety of vinylcyclopropane derivatives. Also, if it were possible to eliminate the need for conducting the process in a stepwise manner, i.e., preforming the anion, and if the need for maintaining strictly anhydrous conditions could be eliminated and if the yield of the desired product could be increased, the process would have even greater utility. These and other advantages are realized by the improved process of this invention.

SUMMARY OF THE INVENTION

We have now quite unexpectedly discovered an improved process for the preparation of vinylcyclopropane derivatives. The process is adaptable to commercial operation and involves reacting, in a fluid state, an alkylating agent, activated methylene compound and alkali metal compound in the presence of a catalyst which is an alkylene oxide derivative. A variety of alkoxylated compounds including polymers of alkylene oxides, primarily ethylene oxide and/or propylene oxide, and reaction products of alkylene oxides with alcohols, phenols and amines can be employed as catalysts. The reaction may be carried out in an inert aprotic organic diluent and it is not necessary to maintain anhydrous conditions.

Alkylating agents useful for the process have from 4 to 26 carbon atoms with a single carbon-carbon double bond. The alkylating agents further contain two groups capable of being nucleophilically displaced, such as halogen, mesyl, tosyl, brosyl, acetate, benzene sulfonate, p-nitrobenzoate or trifluoromethylsulfonate groups, substituted in the allylic positions. Most generally, the alkylating agents will contain from 4 to 8 carbon atoms and are substituted with halogen groups. 1,4-Dichlorobutene-2 and 1,4-dibromobutene-2 are especially useful alkylating agents for the invention.

Suitable activated methylene compounds for use in the process have one or two electron withdrawing groups covalently bonded to a methylene group. Particularly useful activated methylene compounds include: lower alkyl malonates, such as dimethyl malonate, diethyl malonate, dibutyl malonate and diisopropyl malonate; ethyl (N,N-dimethyl-2-aminoethyl) malonate; di(N,N-dimethyl-2-aminoethyl) malonate; ethyl phenylacetate; N,N-dimethyl-2-aminoethyl phenylacetate; acetoacetanilide; methyl acetoacetate; ethyl acetoacetate; ethyl cyanoacetate; 2,4-pentanedione; phenylacetone; malonamide; malonitrile and phenylacetonitrile.

An alkali metal compound and a catalytic amount of an alkylene oxide compound are also employed for the process. Two mols alkali metal compound are required per mol activated methylene compound, however, a molar excess of up to about 20% alkali metal compound can be employed. Especially useful alkali metal compounds are the hydroxides of lithium, sodium and potassium. Trace amounts or substantial quantities of water, up to five parts water per part of activated methylene compound, can be present and may be advantageous. While diluents are not necessary, since an excess of the alkylating agent can be utilized to maintain the reaction mixture in a fluid state and since water can also be present and will also function for this purpose, inert aprotic organic diluents can advantageously be used. The process is conducted as a batch, continuous or semicontinuous operation, typically at atmospheric pressure, while maintaining the temperature between about 1° C. and 200° C., and more preferably, between 5° and 130° C.

Alkoxylated compounds, i.e., alkylene oxide derivatives containing +RO+ repeating units where R is a $C_{2-8}$ alkylene (bivalent hydrocarbon) radical, are effective catalysts for the reaction. The alkylene oxide derivatives may be oxyalkylene polymers obtained by the reaction of an alkylene oxide or alkylene oxide mixture or they may be products obtained by the reaction of an alkylene oxide or alkylene oxide mixture with an alcohol, phenol or amine. Compounds derived from ethylene oxide and propylene oxide or mixtures thereof are particularly useful catalysts for the process of this invention. While the amount of catalyst can range from 0.05 to 25 mol percent, based on the activated methylene compound, it is most usually present from 0.1 to 10 mol percent.

DETAILED DESCRIPTION

The process of this invention relates to the preparation of vinylcyclopropane derivatives. In most general terms, the process involves reacting an alkylating agent with an activated methylene compound using an excess of the alkylating agent as a diluent or in an inert aprotic organic diluent and in the presence of an alkoxylated compound and an alkali metal compound. A wide variety of vinylcyclopropane derivatives are readily prepared by the process of this invention.

Useful alkylating agents for the present process contain from about 4 to 26, and more preferably 4 to 8, carbon atoms, have a single carbon-carbon double bond, and are substituted with two groups which can be nucleophilically displaced. More specifically, the alkylating agents correspond to the general formula

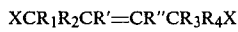

wherein R', R'', $R_1$, $R_2$, $R_3$ and $R_4$ are, independently, hydrogen or an alkyl radical containing from 1 to 4 carbon atoms and X represents a halogen or other leaving group such as mesyl, tosyl, brosyl, acetate, benzene sulfonate, p-nitrobenzoate or trifluoromethyl sulfonate group. Compounds having the latter leaving groups are typically obtained by reaction of the di-hydroxy compound, e.g. 1,4-dihydroxybutene-2, with mesyl chloride, tosyl chloride, brosyl chloride, acetic acid, acetic anhydride, acetyl chloride or the like. Useful halogens include bromine, chlorine or iodine. It is possible to have two different leaving groups substituted on the olefin.

In an especially useful embodiment of this invention, X is chlorine, bromine or iodine, the maximum number of carbon atoms in the molecule is 8 and R', R'', $R_1$, $R_2$, $R_3$ and $R_4$ are hydrogen or methyl. Illustrative olefins of this type include but are not limited to:

1,4-dichlorobutene-2; 1,4-dibromobutene-2; 1-bromo-4-chlorobutene-2;

1,4-dichloro-2-methylbutene-2; 1,4-dibromo-2-methylbutene-2;

1,4-dichloro-2,3-dimethylbutene-2; 1,4-dibromo-2,3-dimethylbutene-2;

1,4-dichloropentene-2; 1,4-dibromopentene-2; 1,4-dichloro-4-methylpentene-2;

1,4-dibromo-4-methylpentene-2; 2,5-dichlorohexene-3; 2,5-dibromohexene-3;

2,5-dichloro-2-methylhexane-3; 2,5-dibromo-2-methylhexene-3;

2,5-dichloro-2,5-dimethylhexene-3; and 2,5-dibromo-2,5-dimethylhexene-3.

1,4-Dichloro- and 1,4-dibromobutene-2 are particularly useful for the present process in view of their commercial availability, reactivity and ability to yield highly useful vinylcyclopropane derivatives with minimal undesirable by-product formation.

As will be evident to those skilled in the art, geometric isomers of the above-described alkylating agents are possible and for the purpose of this invention either the cis- or trans-isomer, or more usually mixtures thereof, can successfully be used in carrying out the reaction. In those instances where the alkylating agent has an appreciabel cis-content some cyclopentene derivatives will generally be formed as a by-product with the vinylcyclopropane derivative.

In addition to using olefins having both substituents allylic to the double bond, it is also possible particularly with halogenated olefins, to utilize compounds which can be isomerized to the desired structure. For example, it is known that 3,4-dichlorobutene-1 and 3,4-dibromobutene-1, can be isomerized to 1,4-dichlorobutene-2 and 1,4-dibromobutene-2, respectively. The isomerization can be carried out prior to charging the reactants to the reaction vessel or, if the process is carried out on a continuous basis, the isomerization can conveniently be carried out in a separate reactor connected to the primary reactor and the isomerized material fed indirectly into the reaction zone as required. It is also possible to isomerize halogenated olefins in situ.

The ability to utilize a variety of alkylating agents imparts versatility to the process in that it permits the preparation of a large number of different cyclopropane compounds. While the cyclopropane compounds obtained by this process will all have a vinyl group in the 2-position, significant variation is possible with the functional group(s) present at the 1-position and with groups substituted on the 3-position of the ring and on the vinyl group. For example, when 1,4-dihalobutene-2 is used the vinyl group and 3-position of the ring will have no alkyl substituents. On the other hand, if 1,4-dichloro-4-methylpentene-2 is employed as the alkylating agent, a mixture of two vinylcyclopropane products is obtained—one of the cyclopropane products having two methyl groups substituted in the 3-position on the ring and the other having two methyl groups substituted at the terminal position of the vinyl group. If in the formula for the alkylating agent set forth above $R_1=R_2=R_3=R_4=Me$, then the vinylcyclopropane compound will have the general structure

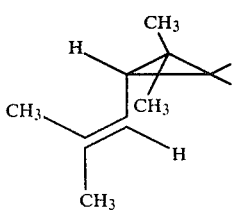

which is the same basic structural moiety present in crysanthemic acid. Compounds containing this structural unit have widely recognized insecticidal and pesticidal properties and to have a process whereby this structure can be readily synthesized in good yield from commonly available and economical starting materials is highly advantageous and most desirable.

Activated methylene compounds reacted with the above-described alkylating agents in accordance with the present improved process have one or two electron withdrawing groups covalently bonded to a methylene group. The presence of the electron withdrawing moieties render the methylene hydrogens sufficiently acidic (labile) so that they are easily removed under the process conditions and the corresponding conjugate base is formed. While for the purpose of this invention it is most desirable to use activated methylene compounds having two electron withdrawing groups, it is possible, when the electron withdrawing character of a particular group is sufficiently strong, to have only one electron withdrawing moiety present. In such a situation the other moiety bonded to the methylene radical can be any group which does not deactivate the methylene hydrogens or otherwise interfere with the reaction. The activated methylene compounds correspond to the general formula

where Y and Z represent the electron withdrawing groups. Y and Z may be the same or they can be different. Most groups known to have electron withdrawing properties are suitable substituents, however, some groups are more desirable than others since they have stronger electron withdrawing capabilities. Availability and the ability to subsequently react the activated methylene compound to obtain useful derivatives or convert it to other useful functions are important criteria in the selection of the particular activated methylene reagent to be used. For the purpose of this invention electron withdrawing groups Y and Z will generally be selected from the following groups:

(a) nitrile ($-C\equiv N$), thionitrile ($-SC\equiv N$) and isothionitrile ($-N=C=S$);
(b) a radical of the formula

wherein $R_5$ is an alkyl, alkeneyl or heteroalkyl radical having from 1 to about 30 carbon atoms, phenyl, an aryl, alkaryl or aralkyl radical having from about 7 to about 24 carbon atoms, a polyoxyalkylene residue such as obtained from a polyoxyalkylene glycol or polyalkoxylated alcohol and which can contain up to about 100 carbon atoms or a radical derived from a heterocyclic alcohol;
(c) a nitrogen-containing radical of the formula

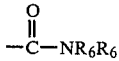

where $R_6$ is hydrogen and/or a radical as defined above for $R_5$ and where the groups ($R_6$) can be the same or different;
(d) an acyl radical of the formula

wherein $R_7$ is an alkyl, alkeneyl or heteroalkyl group having from about 1 to 30 carbon atoms, phenyl or an aryl, alkaryl or aralkyl radical having from 7 to 24 carbon atoms;
(e) an aryl radical including phenyl, fused ring aryls and other fused ring systems wherein at least one of the rings has aromatic character and mono- or multi-substituted groups of these types wherein the substituent(s) is halo, nitro, nitrile, thionitrile, isothionitrile, alkoxyl, phenoxyl, alkyl, aryl, alkaryl, aralkyl, alkeneyl, mercapto and other thio radicals, hydroxyl, fluoroalkyl, or a radical as defined above in (b), (c) and (d);
(f) a five- or six-membered aromatic heterocyclic radical or fused ring system having at least one heteroatom selected from the group sulfur, nitrogen and oxygen and which can be unsubstituted or contain one or more substituents selected from the group halo, nitro, nitrile, thionitrile, isothionitrile, alkoxyl, phenoxyl, alkyl, aryl, alkaryl, aralkyl, alkeneyl, mercapto and other thio radicals, hydroxyl, fluoroalkyl, or a radical as defined above in (b), (c) and (d); and
(g) nitrogen, sulfur or phosphorous radicals containing one or more oxygen atoms selected from the group consisting of nitro, nitroso, sulfones, sulfoxides, esters of sulfonic acid, phosphine oxides and phosphonates.

More specifically electron withdrawing groups X and Y include: radicals of the type (b) where the group $R_5$ is selected from the group consisting of $C_{1-8}$ alkyl, allyl, phenyl, benzyl, naphthyl, 2-phenylethyl, tolyl, xylyl, furfuryl, pyridyl, 2-aminoethyl, N-methyl-2-aminoethyl, N-(2-methoxyethyl)-2-aminoethyl, N-(2-ethoxyethyl)-2-aminoethyl, N-(2-hydroxyethyl)-2-aminoethyl, N,N-dimethyl-2-aminoethyl, N,N-diethyl-2-aminoethyl, N,N-di(2-hydroxyethyl)-2-aminoethyl, N,N-di(2-methoxyethyl)-2-aminoethyl, N,N-di(2-ethoxyethyl)-2-aminoethyl; radicals of the type (c) where $R_6$ is a $C_{1-8}$ alkyl, allyl, phenyl, benzyl, naphthyl, 2-phenylethyl, tolyl, xylyl, furfuryl, pyridyl, 2-hydroxyethyl, 2-methoxyethyl, 2-ethoxyethyl, 2-aminoethyl, N-methyl-2-aminoethyl, N-ethyl-2-aminoethyl, N,N-dimethyl-2-aminoethyl, N,N-diethyl-2-aminoethyl; an acyl radical (d) wherein the group $R_7$ is a $C_{1-18}$ alkyl, allyl, phenyl, benzyl, naphthyl, 2-phenylethyl, tolyl, xylyl, furfuryl and pyridyl; an aryl radical (e) selected from the group phenyl, chlorophenyl, dichlorophenyl, bromophenyl, fluorophenyl, cyanophenyl, thiocyanophenyl, isothiocyanophenyl, methoxyphenyl, phenoxyphenyl, trifluoromethylphenyl, hydroxyphenyl, mercaptophenyl, thiomethylphenyl, nitrophenyl, indanyl, indenyl, naphthyl, dichloronaphthyl, tolyl, xylyl, vinylphenyl, and allylphenyl; and heterocyclic radicals (f) selected from the group furyl, methylfuryl, chlorofuryl, thienyl, pyrryl, pyridyl, methylpyridyl, dimethylpyridyl, benzofuryl, indoyl, benzothienyl, oxazolyl, isooxazolyl, imidazolyl, pyrazolyl, thiazolyl, isothiazolyl, quinolinyl, methylquinolinyl, and isoquinolinyl including all of the various positional isomers thereof.

Especially useful activated methylene compounds due to their ready availability and the fact that highly useful vinylcyclopropane derivatives are obtained therefrom are:

lower alkyl malonates, such as dimethyl malonate, diethyl malonate, dibutyl malonate and diisopropyl malonate;
ethyl (N,N-dimethyl-2-aminoethyl) malonate;
di(N,N-dimethyl-2-aminoethyl) malonate;
ethyl phenylacetate;
N,N-dimethyl-2-aminoethyl phenylacetate;
acetoacetanilide;
methyl acetoacetate;
ethyl acetoacetate;
ethyl cyanoacetate;
2,4-pentanedione;
phenylacetone;
malonamide;
malonitrile; and
phenylacetonitrile.

In accordance with the process of this invention the alkylating agent and activated methylene compound are reacted, either using an excess of the alkylating agent as a diluent or in an inert aprotic organic diluent, in the presence of an alkali metal compound and an alkoxylated compound. In the case where the alkali metal compound is an alkali metal hydroxide and without regard to the R groups of the alkylating agent, the general reaction is described by the equation:

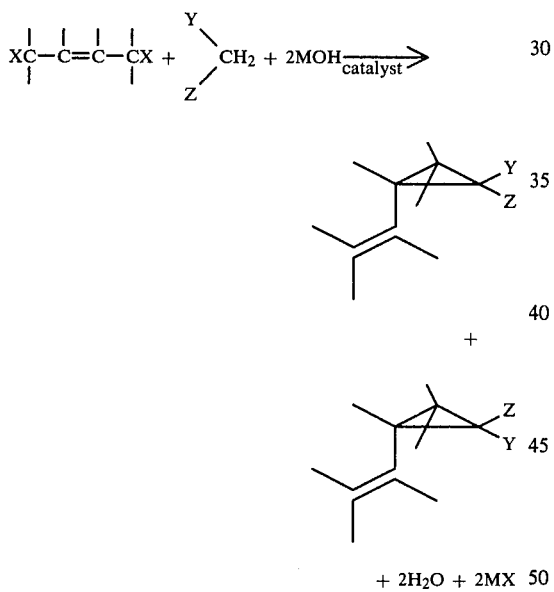

where M represents the alkali metal, X represents the leaving group of the alkylating agent, the groups Y and Z are the electron withdrawing groups of the activated methylene compound and the catalyst is an alkoxylated compound. It will be evident to those skilled in the art that, depending on the substituents present on the alkylating agent, various other geometric and stereo isomers will be obtained.

Catalysts for the reaction are alkylene oxide derivatives containing repeating oxyalkylene units of the formula $-(RO)-$ where R is a bivalent hydrocarbon radical having from 2 to 8 carbon atoms. The oxyalkylene moieties are typically derived from ethylene oxide, propylene oxide, butylene oxide, styrene oxide or mixtures thereof. While the alkylene oxide derivatives may contain up to several hundred oxyalkylene units arranged in a linear manner, the number of repeating oxyalkylene groups most generally does not exceed about 50. Useful alkylene oxide derivatives include poly(oxyalkylene) homopolymers and copolymers produced by the polymerization of the alkylene oxide or alkylene oxide mixture and alkoxylated products obtained by the reaction of an alkylene oxide or mixture thereof with an alcohol, phenol or amine. Compounds of the above types derived from ethylene oxide and/or propylene oxide are particularly useful catalysts for the process. The oxyalkylene catalyst will generally be present in an amount from 0.05 to 25 mol percent based on the activated methylene compound. Most preferably, 0.1 to 10 mol percent catalyst is employed for the process.

Oxyalkylene polymers useful for the process of this invention have the general formula

where R is an alkylene radical having from 2 to 8 carbon atoms, R' is, independently, hydrogen or a $C_{1-4}$ alkyl group and n is an integer such that the molecular weight of the polymer will range from 200 to 25000 and, more preferably, 400 to 15000. Especially useful polymers are those derived from ethylene oxide or propylene oxide, that is, where R is $-CH_2CH_2-$ or

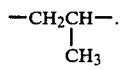

Polyoxyalkylene copolymers, which can be either random copolymers or which may contain block polymer segments, can be obtained by polymerizing two or more alkylene oxide monomers and are also effective catalysts for the present process.

Alkoxylated alcohols and alkoxylated phenols of the formula

wherein R and R' are the same as defined above, $R_1$ is an alkyl group having from 5 to 22 carbon atoms, a cycloalkyl or substituted cycloalkyl group having from 3 to 12 carbon atoms, or an aryl or substituted aryl group having from 6 to 22 carbon atoms and m is an integer from 4 to 35, are also useful catalysts. Alkoxylated amines which can be utilized in the process have the formula

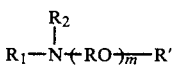

where $R_1$, R, R' and m are the same as defined above and $R_2$ is hydrogen, a radical as defined for R, or the radical $-(RO)_{\overline{m}}R'$. Especially useful alkoxylated phenols, alcohols and amines are those wherein R is a $-CH_2CH_2-$ or

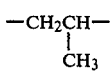

radical and m is an integer from 7 to 24. The alkoxylated alcohols, phenols and amines are prepared in accordance with conventional procedures known to the art and may be derived from a single alkylene oxide or a mixture of alkylene oxides, such as mixtures of ethylene oxide and propylene oxide. In those instances when the oxyalkylene moiety is capped, i.e., R' is an alkyl group, it will preferably be capped with a methyl or ethyl group.

In addition to the alkylene oxide polymers and alkoxylated alcohols, phenols and amines described above, which are the preferred catalysts, still other ethoxylated derivatives may be used to catalyze the reaction. For example, ethoxylated derivatives of mercaptans, polyols, polyol partial esters, carboxylic acids and amides may be utilized. Such compounds are known to the art and processes for their preparation are described in the literature. Illustrative compounds of the foregoing types include: POE(10) dodecyl mercaptan; POE(20) dodecyl mercaptan; POE(20) hexadecyl mercaptan; POE(20) sorbitol; ethoxylated sorbitol hexaoleate; POE(20) sorbitan monooleate; POE(20) sorbitan tristearate; POE(7) lauric acid; POE(23) stearic acid; POE(9) isostearic acid; PGE-200 monolaurate; PEG-400 monostearate; PEG-400 dioleate; and the like. POE denotes poly(oxyethylene) and the number in parenthesis indicates the number of moles of oxyethylene per mole mercaptan, polyol, etc. PEG denotes the average molecular weight of the poly(oxyethylene) moiety.

An alkali metal compound is also required for the process. It is evident from the equation that two mols alkali metal compound are required per mol of activated methylene compound. While it is not necessary, a molar excess of the alkali metal compound, up to about 20%, can be employed. The alkali metal compound can be used as such, that is the solid material added directly to the reaction, or it can be dissolved in water and the resulting aqueous solution employed. While alkali metal hydroxides are most advantageously employed for the process of this invention, other alkali metal compounds such as sodium acetate, sodium carbonate, potassium carbonate, sodium phosphate and the like can be used. Lithium hydroxide, sodium hydroxide and potassium hydroxide are especially useful alkali metal compounds for the process of this invention.

The presence of water is not detrimental to the successful conduct of the reaction which is contrary to heretofore known classical condensation procedures of this type which carefully avoided the presence of water. When alkali metal hydroxides, particularly sodium and potassium hydroxide, are employed there is typically some water associated with these compounds and technical grades of these hygroscopic reagents can contain up to as much as 25% by weight associated water. As the reaction proceeds, additional water is also formed. Water introduced with the reagents or formed during the course of the reaction may be removed by distillation during the reaction or it may be allowed to remain in the reactor. Whereas only small amounts of water are generally present in the reaction mixture, the process may be conducted in the presence of substantial quantities of water—up to 5 parts water per part activated methylene compound.

The ability to conduct the present process in the presence of water is highly advantageous and totally unexpected in view of the prior art teachings of Kierstead et al., Murdock et al. and Den Besten et al. which indicate that water should be excluded in alkylation reactions of this type if optimum yields are to be obtained. It is still even more surprising that with the process of this invention it is not necessary to first form the anion of the activated methylene specie and then very carefully add it to the alkylating agent.

A molar excess of either reactant can be employed depending primarily on the specific reactants used, reaction conditions and whether an inert organic diluent is employed. In usual practice, an excess of the unsaturated alkylating agent is used since this has been found to increase the rate of reaction and minimize the formation of undesirable by-products. It is particularly desirable to employ an excess, often a sizeable excess, of the alkylating agent when the activated methylene compound contains groups, such as ester groups, which are susceptible to hydrolysis. Most generally, the molar ratio of unsaturated alkylating agent to activated methylene compound will range from about 1.01:1 up to about 2:1, even though molar ratios as high as 5:1 can be utilized when the alkylating agent is used as a diluent for the reaction. Preferably, however, the reaction is conducted in an inert aprotic organic diluent at a molar ratio (alkylating agent:activated methylene compound) from about 1.05:1 to about 1.5:1.

For the process the reaction mixture must be in a fluid state. As pointed out above the necessary fluid characteristics can be achieved by using an excess of the alkylating agent, however, it is generally considered most advantageous to carry out the reaction in an inert, aprotic organic diluent. This is especially so in situations where it is desirable to remove water formed during the reaction, such as when the activated methylene compound contains groups which are susceptible to hydrolysis. Removal of some of the water of reaction also simplifies recovery of the resulting vinylcyclopropane product since it facilitates precipitation of inorganic salts which are formed. The use of a diluent which forms an azeotrope with water, such as benzene, toluene, or xylene is especially useful for the removal of excess quantities of water during the course of the reaction. For the purpose of this invention, inert means that the diluent will not significantly react with any of the reagents present under the reaction conditions. Aprotic solvents will not be a source of protons under the reaction conditions.

Preferred inert, aprotic, organic diluents are aromatic, aliphatic or cycloaliphatic hydrocarbons, ethers, esters and chlorinated aliphatic compounds. Preferably the solvents used are liquids to about 10° C. Especially useful diluents within each of the above groups include but are not limited to: benzene, toluene and xylene; pentane, hexane, heptane, cyclohexane, petroleum ether and ligroin; ethyl ether, n-butyl ether, cellosolve, tetrahydrofuran and dioxane; ethyl acetate, butyl acetate and isopropyl acetate; methylene chloride, chloroform, carbon tetrachloride, perchloroethane and ethylene dichloride. Still other aprotic materials such as acetone, methyl ethyl ketone, nitrobenzene, acetonitrile, sulfolane and the like can be used. Compounds such as acetone and acetonitrile, while they might be considered to be activated methylene compounds since they contain an electron withdrawing substituent, can nevertheless be employed as a diluent since the protons of these compounds are not as labile as the protons of the reactant under the conditions of the process and therefore they will not significantly react with the alkylating agent.

The amount of diluent is not critical as long as the reaction mixture is sufficiently fluid to permit the reaction to occur. Too viscous a reaction mixture will suppress the reaction as will the use of too large a volume of the diluent. While about 0.25 up to about 10 volumes diluent can be present per volume of combined reactants (alkylating agent, activated methylene compound and alkali metal compound), more usually, 0.5 to 5.0 volumes diluent per volume of reactants is used for the process.

The alkylation reaction is exothermic and the temperature will generally be maintained with agitation between about 1° C. to about 200° C. and, more preferably, between about 5° C. to about 130° C. The method of agitation is not critical and conventional methods can be used for this purpose. While the reaction is conveniently conducted at ambient pressure, it is possible to carry out the reaction at sub-atmospheric pressure or at super-atmospheric pressure. Batch, continuous or semi-continuous operation is possible with the present process and with proper equipment modifications the diluent can be recycled. The catalyst may also be recycled for repeated use. This is conveniently accomplished by removing the inorganic salts by filtration or water washing and then distilling to remove the vinylcyclopropane product. The residue from the distillation can be used in subsequent reactions with good results. The manner of addition of the reagents is not critical. Customarily, the alkylating agent, activated methylene compound and catalyst compound are combined (in an inert diluent if one is used) and the alkali metal hydroxide added thereto or the inert diluent, catalyst and alkali metal hydroxide combined and a solution of the alkylating agent and activated methylene compound charged to the reactor with stirring.

Compounds obtained by the process of this invention can be further reacted to obtain additional useful compounds. They are useful monomers for the preparation of oligomers which can be used as such or further polymerized by light, organic peroxides, or other normal means to generate polymers which have enhanced plasticity, pigment dispersibility and film forming characteristics. Vinylcyclopropane derivatives are also useful in insecticidal and pesticidal applications. They are useful agricultural chemicals for controlling plant functions by inhibiting or enhancing growth, flower sex change, production of more fruit, root growth, etc. Compounds obtained by the process of this invention are also useful for the preparation of prostoglandins, cyclic fungicides, pyrethroid type insecticides and the like.

The following examples illustrate the various aspects of this invention more fully. Numerous other modifications are possible and within the scope of the present invention, however, as will be evident to those skilled in the art.

EXAMPLE I

To illustrate the preparation of diethyl 2-vinylcyclopropane-1,1-dicarboxylate in accordance with the process of this invention, the following experiment was conducted. To a glass reactor equipped with a stirrer were charged 50 ml. methylene dichloride, 6.86 g (0.11 mol) potassium hydroxide powder and 3 g ethoxylated lauryl alcohol containing an average of 23 repeating ethylene oxide units. Trans-1,4-dichlorobutene-2 (6.25 g; 0.05 mol) and diethyl malonate (8 g; 0.05 mol) were combined and slowly added to the reactor with stirring over a 5 minute period during which time a mild exotherm (28° C.) was observed. Stirring was continued and samples periodically removed for gas chromatographic analysis to follow the progress of the reaction.

The reaction was terminated after about 2 hours, when chromatographic analysis indicated the reaction was essentially complete, and the reaction mixture filtered through alumina silicate. After removal of the diluent on a rotary evaporator, the reaction product was vacuum distilled and 7.18 g (50.52% yield) diethyl 2-vinylcyclopropane-1,1-dicarboxylate (boiling point 64°–66° C. at 0.5 mm Hg; $n_D^{27° C.}$ 1.4512) obtained. Infrared and proton nmr spectra were consistent with the desired structure. Similar results are obtained when sodium hydroxide, trans-1,4-dibromobutene-2 and di-n-butyl-malonate are reacted under similar conditions using the ethoxylated POE(23) lauryl alcohol catalyst. Also, good results are obtained when benzene is employed as the diluent and the reaction is carried out at 80° C. with water being azeotropically removed from the reaction mixture during the course of the reaction.

EXAMPLE II

To demonstrate the versatility of the process, 16 g (0.1 mol) diethyl malonate and 62.55 g of a block copolymer of ethylene oxide and polypropylene oxide having an average molecular weight of about 13,300 (Pluronic ® 127) were charged to a reactor. Methylene dichloride (100 mls.) and 11.2 g solid potassium hydroxide (90%) were added and the mixture vigorously agitated while maintaining the temperature at or below 35° C. The 1,4-dichlorobutene-2 (12.4 g; 0.1 mol) was then added over a 5 minute period. About 22% conversion to diethyl 2-vinylcyclopropane-1,1-dicarboxylate was obtained after one hour of reaction. The reaction was continued to obtain essentially complete conversion of the reactants to the desired vinylcyclopropane product.

EXAMPLE III 1,4-Dibromobutene-2 (21.4 g), 11.2 g solid 90 percent potassium hydroxide and 50 mls methylene dichloride were charged to a reactor and a mixture of 16 g diethyl malonate and 2.13 poly(propylene glycol) having an average molecular weight of about 425 added slowly while the reaction mixture was vigorously agitated with cooling. After completion of the addition (approx. 15 minutes) the reaction mixture was agitated for one hour. Workup of the reaction product gave 54.1% yield diethyl 2-vinylcyclopropane-1,1-dicarboxylate.

EXAMPLE IV

Ethyl acetoacetate was reacted with 1,4-dichlorobutene-2 in a manner similar to that described in Example III using a poly(oxypropylene) catalyst. For the reaction, 5.6 g potassium hydroxide and 50 mls. methylene dichloride were combined in the reaction vessel and ethyl acetoacetate (6.5 g), the poly(propylene glycol) catalyst (1.06 g) and 20 mls. methylene dichloride rapidly added with vigorous stirring. 1,4-Dibromobutene-2 (10.7 g) was then added via a solids addition funnel while maintaining the temperature at about 35° C. Seventy-four percent yield 1-carboethoxy-1-methylketo-2-vinylcyclopropane was obtained. The product had a boiling point of 58° C. at 0.85 mm Hg, refractive index ($n_D^{25}$) of 1.4707, and the structure was confirmed by infrared and proton nmr spectroscopy. When the process is repeated reacting 1,4-dichlorobutene-2 with phenylacetonitrile, ethyl phenylacetate and acetoacetanilide, 1-cyano-1-phenyl-2-vinylcyclopropane, 1-carboethoxy-1-phenyl-2-vinylcyclopropane, and 1-carboxanilido-1-methylketo-2-vinylcyclopropane are respectively obtained.

EXAMPLE V

Diethyl malonate was reacted with 1,4-dibromobutene-2 obtained from the isomerization of 3,4-dibromobutene-1. An ethoxylated amine catalyst was employed for the process. For this reaction 5.6 g potassium hydroxide, 100 mls. methylene dichloride and 8 g diethyl malonate were combined in the reactor with 6.21 g ethoxylated (50 E.O.) stearyl amine. The mixture was stirred and 10.7 g 1,4-dibromobutene-2 added while maintaining the temperature at 30° C. by means of a cooling bath. When the addition was complete the reaction was maintained at 30° C. for one hour and about 15% conversion to the desired product obtained. The reaction was continued with heating to obtain diethyl 2-vinylcyclopropane-1,1-dicarboxylate in good yield. Comparable results are obtained using sodium hydroxide and lithium hydroxide with 1,4-dichlorobutene-2.

EXAMPLE VI

To a reactor containing 5.6 g potassium hydroxide and 60 mls. methylene dichloride were added 6.5 g ethyl acetoacetate and 1.33 g ethoxylated (9 E.O.) nonylphenol. The mixture was agitated and 10.7 g 1,4-dibromobutene-2 slowly added while maintaining the temperature at 30°–35° C. The reaction was continued with stirring at 30° C. for one hour after which time 74% yield 1-carboethoxy-1-methylketo-2-vinylcyclopropane was obtained. Similar results are obtained when the reaction is repeated using 1,4-dichlorobutene-2 and 1,4-diacetoxybutene-2.

I claim:

1. A process for the preparation of vinylcyclopropane compounds which comprises reacting in a fluid state with agitation and at a temperature between 1° C. and 200° C.:
   (a) an alkylating agent having from 4 to 26 carbon atoms and a single carbon-carbon double bond and substituted with two groups capable of being nucleophically displaced;
   (b) an activated methylene compound having one or two electron withdrawing groups covalently bonded to the methylene group; and
   (c) an alkali metal compound; said reaction conducted in the presence of 0.05 to 25 mol percent, based on the activated methylene compound, of an alkylene oxide derivative containing repeating units of the formula $-(RO)-$ where R is a bivalent hydrocarbon radical having from 2 to 8 carbon atoms.

2. The process of claim 1 wherein the alkylene oxide derivative is (a) an oxyalkylene polymer of the formula $$R'O-(RO)_{\overline{m}}R'$$

where R is an alkylene radical having from 2 to 8 carbon atoms, R' is hydrogen or a $C_{1-4}$ alkyl group and n is an integer such that the molecular weight of the polymer is between 200 or 25000; (b) an alkoxylated alcohol or phenol of the formula $$R_1O-(RO)_{\overline{m}}R'$$

where R and R' are the same as defined above for (a), m is an integer from 4 to 35, and $R_1$ is a $C_{5-22}$ alkyl group, $C_{3-12}$ cycloalkyl or substituted cycloalkyl group, or aryl or substituted aryl having from 6 to 22 carbon atoms; or (c) an alkoxylated amine of the formula $$R_1 N\!\!-\!\!(RO)_{\overline{m}}\!\!-\!\!R' \atop |\phantom{R_1 N\!\!-\!\!(RO)_{\overline{m}}}R_2$$

where $R_1$, R, R' and m are the same as defined above for (a) and (b) and $R_2$ is hydrogen, a radical as defined for R, or the group $-(RO)_{\overline{m}}R'$.

3. The process of claim 2 wherein the alkali metal compound is a hydroxide of lithium, sodium or potassium; the alkylating agent has the formula $XCR_1R_2CR'=CR''CR_3R_4X$ were X is halogen, mesyl, tosyl, brosyl, acetate, benzene sulfonate, p-nitrobenzoate or trifluoromethylsulfonate and R', R'', $R_1$, $R_2$, $R_3$ and $R_4$ are hydrogen or an alkyl group containing from 1 to 4 carbon atoms; and the electron withdrawing groups of the activated methylene compound are selected from the group
   (a) nitrile, thionitrile, isothionitrile;
   (b) a radical of the formula $$-\underset{\underset{O}{\|}}{C}-OR_5$$

where $R_5$ is an alkyl, alkeneyl or heteroalkyl radical having from 1 to about 30 carbon atoms, phenyl, an aryl, alkaryl or aralkyl radical having from about 7 to 24 carbon atoms, a polyoxyalkylene residue such as obtained from a polyoxyalkylene glycol or polyalkoxylated alcohol and which can contain up to about 100 carbon atoms or a radical derived from a heterocyclic alcohol;
   (c) a nitrogen-containing radical of the formula $$-\underset{\underset{O}{\|}}{C}-NR_6R_6$$

were $R_6$ is hydrogen and/or a radical as defined for $R_5$;
   (d) an acyl radical of the formula $$-\underset{\underset{O}{\|}}{C}R_7$$

wherein $R_7$ is an alkyl, alkeneyl or heteroalkyl group having from about 1 to 30 carbon atoms, phenyl or an aryl, alkaryl or aralkyl radical having from 7 to 24 carbon atoms;
   (e) an aryl radical including phenyl, fused ring aryls and other fused ring systems wherein at least one of the rings has aromatic character and mono- or multi-substituted groups of these types wherein the substituent(s) is halo, nitro, nitrile, thionitrile, isothionitrile, alkoxyl, phenoxyl, alkyl, aryl, alkaryl, aralkyl, alkeneyl, mercapto and other thio radicals, hydroxyl, fluoroalkyl, or a radical as defined for (b), (c) and (d);
   (f) a five- or six membered aromatic heterocyclic radical or fused ring system having at least one heteroatom selected from the group sulfur, nitrogen and oxygen and which can be unsubstituted or contain one or more substituents selected from the group, halo, nitro, nitrile, thionitrile, isothionitrile, alkoxyl, phenoxyl, alkyl, aryl, alkaryl, aralkyl, alkeneyl, mercapto and other thio radicals, hydroxyl, fluoroalkyl, or a radical as defined for (b), (c) and (d); and (g) nitrogen, sulfur or phosphorous radicals containing one or more oxygen atoms selected from the group consisting of nitro, nitroso, sulfones, sulfoxides, esters of sulfonic acid, phosphine oxides and phosphonates.

4. The process of claim 3 wherein for the alkylene oxide derivatives (a), (b) and (c) R is predominantly —CH₂CH₂— or

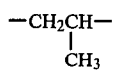

and R' is a methyl or ethyl group.

5. The process of claims 2, 3 or 4 wherein the reaction is conducted in an inert aprotic organic diluent, said diluent selected from aromatic, aliphatic or cycloaliphatic hydrocarbons, ethers, esters or chlorinated compounds and present in an amount from 0.25 up to 10 volumes per volume of reactants.

6. The process of claim 5 wherein the inert aprotic organic diluent forms an azeotrope with water.

7. The process of claim 5 wherein the mol ratio of alkylating agent to activated methylene compound ranges from 1.01:1 to 2:1, the alkylating agent contains 4 to 8 carbon atoms and in the formula for the alkylating agent X is chlorine or bromine and R', R'', R₁, R₂, R₃ and R₄ are hydrogen or methyl.

8. The process of claim 7 wherein the alkali metal hydroxide is employed at up to about 20% molar excess and the reaction is conducted in the temperature range 5° C. to 130° C.

9. The process of claim 8 wherein the alkylene oxide derivative is present in an amount from 0.1 to 10 mol percent; the alkylating agent is an unsaturated halogenated olefin selected from the group consisting of 1,4-dichlorobutene-2, 1,4-dibromobutene-2, 1-bromo-4-chlorobutene-2, 1,4-dichloro-2-methylbutene-2, 1,4-dibromo-2-methylbutene-2, 1,4-dichloro-2,3-dimethylbutene-2, 1,4-dibromo-2,3-dimethylbutene-2, 1,4-dichloropentene-2, 1,4-dibromopentene-2, 1,4-dichloro-4-methylpentene-2, 1,4-dibromo-4-methylpentene-2, 2,5-dichlorohexene-3, 2,5-dibromohexene-3, 2,5-dichloro-2-methylhexene-3, 2,5-dibromo-2-methylhexene-3, 2,5-dichloro-2,5-dimethylhexene-3, and 2,5-dibromo-2,5-dimethylhexene-3; and the activated methylene compound is selected from the group consisting of dimethyl malonate, diethyl malonate, dibutyl malonate, diisopropyl malonate, ethyl (N,N-dimethyl-2-aminoethyl) malonate, di(N,N-dimethyl-2-aminoethyl) malonate, ethyl phenylacetate, N,N-dimethyl-2-aminoethyl phenylacetate, acetoacetanilide, methylacetoacetate, ethylacetoacetate, ethyl cyanoacetate, 2,4-pentanedione, phenylacetone, malonamide, malonitrile and phenylacetonitrile.

* * * * *